US006927306B2

(12) United States Patent
Zaima

(10) Patent No.: US 6,927,306 B2
(45) Date of Patent: Aug. 9, 2005

(54) PROCESS FOR PRODUCING HYDROGENATED AROMATIC POLYCARBOXYLIC ACID AND PROCESS FOR PRODUCING HYDROGENATED AROMATIC POLYCARBOXYLIC ANHYDRIDE

(75) Inventor: Fumiya Zaima, Okayama (JP)

(73) Assignee: Mitsubishi Gas Chemical Company, Inc., Tokyo (JP)

( * ) Notice: Subject to any disclaimer, the term of this patent is extended or adjusted under 35 U.S.C. 154(b) by 129 days.

(21) Appl. No.: 10/329,510

(22) Filed: Dec. 27, 2002

(65) Prior Publication Data

US 2003/0149297 A1 Aug. 7, 2003

(30) Foreign Application Priority Data

Dec. 28, 2001 (JP) ....................................... 2001-400207
Jan. 23, 2002 (JP) ....................................... 2002-013980

(51) Int. Cl.$^7$ ........................ C07C 61/00; C07D 307/77
(52) U.S. Cl. ...................................... 562/400; 549/234
(58) Field of Search ................................ 562/400, 509; 549/234

(56) References Cited

U.S. PATENT DOCUMENTS

| | | | |
|---|---|---|---|
| 2,888,484 | A | 5/1959 | Dehm et al. |
| 3,141,036 | A | 7/1964 | Winstrom et al. |
| 4,754,064 | A | 6/1988 | Lillwitz |
| 5,412,108 | A | 5/1995 | Fisher |

FOREIGN PATENT DOCUMENTS

GB 967919 8/1964

OTHER PUBLICATIONS

Freifelder, et al., "Low–Pressure Hydrogenation of Some Benzenepolycarboxylic Acids with Rhodium Catalyst", Journal of Organic Chemistry, vol. 31, pp. 3438–3439, 1966.

Primary Examiner—Paul J. Killos
(74) Attorney, Agent, or Firm—Antonelli, Terry, Stout & Kraus, LLP

(57) ABSTRACT

Disclosed are processes for industrially advantageously producing at a good yield respectively, a hydrogenated aromatic polycarboxylic acid and an acid anhydride thereof each having a high purity. The present invention provides processes for producing a hydrogenated aromatic polycarboxylic acid by (1) hydrogenating an aromatic polycarboxylic acid at a hydrogen partial pressure of 1 MPa or more by a batch system in the presence of a catalyst containing rhodium and palladium in a proportion of 0.5 to 10 parts by weight per 100 parts by weight of the aromatic polycarboxylic acid and by (2) feeding an aromatic polycarboxylic acid to a filling bed of a catalyst containing rhodium and palladium at a WHSV of 1 to 100 h$^{-1}$ to hydrogenate it at a hydrogen partial pressure of 1 MPa or more by a continuous flow system, and a process for producing a hydrogenated aromatic polycarboxylic anhydride by subjecting the hydrogenated aromatic polycarboxylic acid obtained by the processes described above to dehydration reaction with acetic anhydride of 0.64 to 5.7 times mole based on a carboxyl group of the hydrogenated aromatic polycarboxylic acid.

22 Claims, No Drawings

PROCESS FOR PRODUCING HYDROGENATED AROMATIC POLYCARBOXYLIC ACID AND PROCESS FOR PRODUCING HYDROGENATED AROMATIC POLYCARBOXYLIC ANHYDRIDE

BACKGROUND OF THE INVENTION

1. Field of the Invention

The present invention relates to a process for producing a hydrogenated aromatic polycarboxylic acid in which an aromatic ring of an aromatic polycarboxylic acid is hydrogenated and a process for producing a hydrogenated aromatic polycarboxylic anhydride. More specifically, the present invention relates to processes for industrially advantageously producing a hydrogenated aromatic polycarboxylic acid and an acid anhydride thereof each having a high purity at a good yield respectively, which are used as a raw material for functional polyimides having properties such as transparency and solvent solubility and a curing agent for functional epoxy resins having transparency.

2. Description of the Related Arts

A process in which an aromatic polycarboxylic acid, an alkaline metal acid thereof or an ester derivative thereof is nucleus-hydrogenated is known as a process for producing a hydrogenated aromatic polycarboxylic acid.

Available are, for example, a process in which pyromellitic acid or tetraethyl pyromellitate is hydrogenated on the conditions of a hydrogen pressure of 200 atm, a temperature of 150° C. and a reaction time of 3 days using a Raney nickel catalyst (Journal of Organic Chemistry, vol. 28, p. 1770 (1963)) and a process in which a pyromellitic acid aqueous solution is hydrogenated on the conditions of a hydrogen pressure of 2.7 atm, a temperature of 60° C. and a reaction time of 1.5 hours in the presence of a rhodium catalyst (Journal of Organic Chemistry, vol. 31, p. 3438 (1966)). Also, known is a process in which pyromellitic dianhydride is esterified with 1-propanol and in which an ester derivative thereof is hydrogenated at a hydrogen pressure of 100 kg/cm$^2$ G and a temperature of 130° C. for 2.5 hours in the presence of a ruthenium catalyst (Japanese Patent Application Laid-Open No. 325196/1996 and Japanese Patent Application Laid-Open No. 325201/1996). Further, known as well is a process in which trimellitic acid is dissolved in a mixed solvent of tetrahydrofuran and water and hydrogenated at a hydrogen pressure of 1400 psig and a temperature of 60° C. for 4 hours in the presence of a 5 weight % rhodium catalyst carried on carbon having a surface area of 940 m$^2$/g or more (U.S. Pat. No. 5,412,108).

In the fields of functional polyimide and a functional epoxy resin curing agent in which a hydrogenated aromatic polycarboxylic acid is used as a raw material, raw materials having less impurities are desired. It is difficult to separate an unreacted aromatic polycarboxylic acid from a hydrogenated aromatic polycarboxylic acid by crystallization, and therefore the conversion rate in hydrogenation reaction has to be elevated to 99.8% or more in order to obtain a hydrogenated aromatic polycarboxylic acid having a high purity. Further, it is required to reduce the contents of alkali metals, halogens and ashes.

However, in the process described in, for example, Journal of Organic Chemistry, vol. 28, p. 1770 (1963) described above, unavoidable is contamination caused by inorganic matters such as alkali metal originating in alkali used when dissolving the raw materials and chlorine originating in an acid used when recovering 1,2,4,5-cyclohexanetetracarboxylic acid from the reaction liquid.

Also, in the process described in Journal of Organic Chemistry, vol. 31, p. 3438 (1966) described above, the conversion rate and the selectivity in hydrogenation reaction are not satisfactory, and unreacted pyromellitic acid remains. It is difficult to separate unreacted pyromellitic acid from nucleus-hydrogenated 1,2,4,5-cyclohexanetetracarboxylic acid by crystallization, and therefore the conversion rate in hydrogenation reaction has to be elevated to 99.8% or more in order to obtain 1,2,4,5-cyclohexane-tetracarboxylic acid having a high purity.

Further, in the process via an ester derivative disclosed in Japanese Patent Application Laid-Open No. 325196/1996 and Japanese Patent Application Laid-Open No. 325201/1996, the reaction step is long, and the reaction apparatus is complicated, so that the above process is not necessarily advantageous in terms of a production cost.

In addition thereto, metals such as iron, chromium, nickel and molybdenum eluted from a reaction apparatus are considered to be impurities, but they can be avoided by making the reaction apparatus out of a material having a strong acid resistance.

On the other hand, when a catalyst was repeatedly used in nucleus-hydrogenating an aromatic polycarboxylic acid to produce a hydrogenated aromatic polycarboxylic acid, observed was the phenomenon that an activity of the catalyst was reduced in several frequencies and that the conversion rate in hydrogenation reaction was deteriorated to a large extent. In respect to the activation of a catalyst used for hydrogenation reaction, it is described in U.S. Pat. No. 5,412,108 that impurities can be removed by washing the catalyst with polar solvents such as ethers, esters, aliphatic carboxylic acids and ketones and aromatic compounds such as benzene, toluene, xylene to make it possible to repeatedly use the catalyst. However, washing the catalyst with a solvent which is different from the reaction solvent is not necessarily advantageous as an industrial process. Further, it is described in Japanese Patent Application Laid-Open No. 159059/1989 that a ruthenium hydrogenation catalyst which is used for partial nucleus-hydrogenation reaction of an aromatic compound and reduced in an activity can be reproduced by bringing it into contact with oxygen in a liquid phase, for example, in a state in which a catalyst is dispersed in a suitable liquid or a state in which the catalyst is impregnated with the liquid, that is, in a state in which at least the surface of the catalyst is covered with the liquid.

On the other hand, it is known that an acid anhydride is obtained by subjecting an aromatic polycarboxylic acid to dehydration reaction. For example, 1,2,4,5-cyclohexanetetracarboxylic dianhydride is produced by subjecting 1,2,4,5-cyclohexanetetracarboxylic acid to cyclodehydration.

In general, a method carrying out heat treatment or a method using a dehydrating agent is used for dehydrating and ring-closing carboxyl groups which are adjacent and bonded to an aromatic or non-aromatic (alicyclic) six-membered ring to synthesize a cyclic acid anhydride. Known as well is a method in which refluxing by heating is carried out in the coexistence of an acid anhydride such as acetic anhydride and propionic anhydride as the dehydrating agent. In this case, hydrocarbons, halogenated hydrocarbons, esters, ketones, ethers and aliphatic acids each having a boiling point of 50° C. or higher may be added as a solvent.

A method in which refluxing by heating is carried out using acetic anhydride is known as a method for subjecting 1,2,4,5-cyclohexane-tetracarboxylic acid to cyclodehydration (refer to Japanese Patent Publication No. 23339/1995 and Japanese Patent Application Laid-Open No. 325196/1996).

In the field of functional polyimides in which a hydrogenated aromatic polycarboxylic acid anhydride is used as a raw material, the raw materials which are reduced in impurities and have a high purity are desired.

However, mere heat treatment of, for example, 1,2,4,5-cyclohexanetetracarboxylic acid results in coloring of the crystals. Further, as described in Japanese Patent Application Laid-Open No. 325196/1996, if 1,2,4,5-cyclohexanetetracarboxylic acid is subjected to cyclodehydration using acetic anhydride of a 10 times amount (weight ratio) based on 1,2,4,5-cyclohexanetetracarboxylic acid, dehydration reaction goes on without causing any problems, but because of a high solubility of 1,2,4,5-cyclohexanetetracarboxylic dianhydride which is the intended product in acetic anhydride, the crystals of the above anhydride can not easily be recovered.

In order to solve this, it is considered to elevate the recovering rate of 1,2,4,5-cyclohexane-tetracarboxylic dianhydride crystals by a method such as condensing a reaction solution and condensing a mother liquid after separating the crystals, but it is disadvantageous as an industrial production process in terms of that the number of the equipments is increased and that the process is lengthened, and the crystals of 1,2,4,5-cyclohexanetetracarboxylic dianhydride are colored or impurities are introduced into the crystals of the acid anhydride to cause a reduction in the crystal purity.

Thus, it has been difficult in conventional techniques to obtain industrially advantageously a hydrogenated aromatic polycarboxylic anhydride.

SUMMARY OF THE INVENTION

Under such circumstances, a first object of the present invention is to provide a process for producing industrially advantageously a hydrogenated aromatic polycarboxylic acid having a high purity at a high yield, and a second object of the present invention is to provide a process for producing efficiently a hydrogenated aromatic polycarboxylic acid anhydride having a high purity at a low cost by a simple process.

Thus, intensive researches repeated by the present inventor in order to achieve the objects described above resulted in finding that the first object can be achieved by hydrogenating an aromatic polycarboxylic acid on the condition of a hydrogen pressure of some value or more by a batch system in the presence of a prescribed amount of a specific noble metal catalyst or by feeding an aromatic polycarboxylic acid to a filling bed of a specific noble metal catalyst at a prescribed weight hour space velocity (WHSV) to hydrogenate it on the condition of a hydrogen pressure of some value or more by a continuous flow system. Further, it has been found that in these processes, activation treatment of the catalyst used for hydrogenation makes it possible to maintain a high reaction conversion rate thereof even if it is repeatedly used for hydrogenation.

Further, the present inventor has found that the second object can be achieved by using an acid hydrogenated by the process described above as the hydrogenated aromatic polycarboxylic acid and optimizing a use proportion of this hydrogenated aromatic polycarboxylic acid to acetic anhydride and by using preferably glacial acetic acid as a reaction solvent.

The present invention has been completed based on such knowledge.

That is, the first object of the present invention can be achieved by:
(1) a process for producing a hydrogenated aromatic polycarboxylic acid, wherein in hydrogenating an aromatic polycarboxylic acid by a batch system, the aromatic polycarboxylic acid is hydrogenated at a hydrogen partial pressure of 1 MPa or more in the presence of a catalyst containing noble metal comprising rhodium or palladium or both of them in a proportion of 0.5 to 10 parts by weight per 100 parts by weight of the aromatic polycarboxylic acid, and
(2) a process for producing a hydrogenated aromatic polycarboxylic acid, wherein in hydrogenating an aromatic polycarboxylic acid by a continuous flow system, the aromatic polycarboxylic acid is fed to a filling bed of a catalyst containing noble metal comprising rhodium or palladium or both of them at a velocity of 1 to 100 weight parts/hr per weight part of the noble metal described above to hydrogenate it at a hydrogen partial pressure of 1 MPa or more.

Also, in the production processes of (1) and (2) described above, the catalyst used for hydrogenation which is subjected to activation treatment can be reused as the catalyst.

Next, the second object of the present invention can be achieved by:
(3) a process for producing a hydrogenated aromatic polycarboxylic anhydride, wherein in producing an acid anhydride by dehydration reaction, used as the above hydrogenated aromatic polycarboxylic acid is one obtained by hydrogenating an aromatic polycarboxylic acid at a hydrogen partial pressure of 1 MPa or more by a batch system in the presence of a catalyst containing noble metal comprising rhodium or palladium or both of them in a proportion of 0.5 to 10 parts by weight per 100 parts by weight of the aromatic polycarboxylic acid; and the above hydrogenated aromatic polycarboxylic acid is subjected to dehydration reaction with acetic anhydride of 0.64 to 5.7 times mole based on a carboxyl group of the hydrogenated aromatic polycarboxylic acid, and
(4) a process for producing a hydrogenated aromatic polycarboxylic anhydride, wherein in producing an acid anhydride by dehydration reaction, used as the above hydrogenated aromatic polycarboxylic acid is one obtained by feeding an aromatic polycarboxylic acid to a filling bed of a catalyst containing noble metal comprising rhodium or palladium or both of them at a velocity of 1 to 100 weight parts/hr per weight part of the noble metal described above to hydrogenate it at a hydrogen partial pressure of 1 MPa or more by a continuous flow system; and the above hydrogenated aromatic polycarboxylic acid is subjected to dehydration reaction with acetic anhydride of 0.64 to 5.7 times mole based on a carboxyl group of the hydrogenated aromatic polycarboxylic acid.

Also, in the production processes of (3) and (4) described above, the dehydration reaction is preferably carried out in a glacial acetic acid solvent.

DESCRIPTION OF THE PREFRRED EMBODIMENTS

First, the process for producing the hydrogenated aromatic polycarboxylic acid shall be explained. In the present invention, the hydrogenated aromatic polycarboxylic acid means one obtained by hydrogenating an aromatic ring of an aromatic polycarboxylic acid and includes a compound in which an aromatic ring is completely hydrogenated to have a skeleton of a cyclohexane ring structure and a compound in which an aromatic ring is partially hydrogenated to have a cyclohexene or cyclohexadiene skeleton.

In the process for producing the hydrogenated aromatic polycarboxylic acid according to the present invention, the aromatic polycarboxylic acid used as the raw material may be a compound in which two or more carboxyl groups are introduced onto an aromatic ring and shall not specifically be restricted, and it can suitably be selected from various compounds according to the use purposes thereof.

Capable of being given as the examples of this aromatic polycarboxylic acid are dicarboxylic acids such as terephthalic acid, isophthalic acid, phthalic acid, 2,3-naphthalenedicarboxylic acid, 2,6-naphthalenedicarboxylic acid, 1,4-naphthale-nedicarboxylic acid, 1,8-naphthalenedicarboxylic acid, anthracenedicarboxylic acid, 4,4'-benzophenone-dicarboxylic acid, 3,3'-biphenyldicarboxylic acid, 4,4'-biphenyldicarboxylic acid, 3,3'-biphenylether-dicarboxylic acid, 4,4'-biphenyletherdicarboxylic acid and 4,4'-binaphthyldicarboxylic acid; tricarboxylic acids such as trimellitic acid, 1,2,3-benzenetricarboxylic acid, trimesic acid, 2,5,7-naphthalenetricarboxylic acid and 1,2,4-naphthalene-tricarboxylic acid; tetracarboxylic acids such as pyromellitic acid, 3,3',4,4'-benzophenone-tetracarboxylic acid, 2,2',3,3'-benzophenone-tetracarboxylic acid, 2,3,3',4'-benzophenone-tetracarboxylic acid, 3,3',4,4'-biphenyl-tetracarboxylic acid, 2,2',3,3'-biphenyl-tetracarboxylic acid, 2,3,3',4'-biphenyl-tetracarboxylic acid, 4,4'-oxydiphthalic acid, diphenylmethanetetracarboxylic acid, 1,4,5,8-naphthalenetetracarboxylic acid, 1,2,5,6-naphthalenetetracarboxylic acid, 2,3,6,7-naphthalenetetracarboxylic acid, 3,4,9,10-perylenetetracarboxylic acid, anthracene-tetracarboxylic acid and 4,4'-(hexafluoro-isopropylidene) diphthalic acid; and polycarboxylic acids such as benzenepentacarboxylic acid and benzenehexacarboxylic acid.

Among them, pyromellitic acid, trimellitic acid and trimesic acid are suited from the viewpoint of an industrial utility value of the resulting hydrogen compound. The quality of these aromatic polycarboxylic acids may be grades which are usually available in the market.

A reaction solvent is suitably used for the hydrogenation reaction in the present invention, and water is particularly preferred. The aromatic polycarboxylic acid of the raw material may be either dissolved or dispersed in a solvent. In this case, a concentration of the aromatic polycarboxylic acid is preferably 5 to 50% by weight, more preferably 10 to 40% by weight.

The hydrogenated aromatic polycarboxylic acid may be crystallized by cooling or condensing after the hydrogenation reaction, and a mother liquid obtained by separating the crystal may be used by circulating. A proportion of sending the mother liquid back to the reactor can suitably be determined according to an accumulation degree of impurities in the system.

In the present invention, the catalyst containing noble metal comprising rhodium or palladium or both of them is used as a hydrogenation reaction catalyst, and a catalyst prepared by carrying the noble metal described above on a carrier is particularly preferred. Carbon and alumina are preferred as the carrier. The catalyst shall not specifically be restricted in a form, and powder, granule and pellet for a fixed bed are selected according to the hydrogenation reaction. An amount thereof carried on the carrier is preferably 0.5 to 30% by weight, more preferably 0.5 to 10% by weight based on the whole amount of the catalyst.

In the production process of the present invention, a reaction mode includes two modes of a batch system (including a semi-continuous system) and a continuous flow system.

First, in the batch system, the aromatic polycarboxylic acid is hydrogenated at a hydrogen partial pressure of 1 MPa or more in the presence of a catalyst containing noble metal comprising rhodium or palladium or both of them in a proportion of 0.5 to 10 parts by weight per 100 parts by weight of the aromatic polycarboxylic acid. If the amount of the noble metal described above is less than 0.5 part by weight per 100 parts by weight of the aromatic polycarboxylic acid, the hydrogenation reaction does not sufficiently go on. Also, an upper limit of 10 parts by weight is enough, and if exceeding it, it is economically rather disadvantageous. A preferred use amount of the above noble metal falls in a range of 0.5 to 5.0 parts by weight per 100 parts by weight of the aromatic polycarboxylic acid.

On the other hand, if the hydrogen partial pressure is less than 1 MPa, the desired reaction conversion rate is not obtained, and the objects of the present invention shall not be achieved. The preferred hydrogen partial pressure falls in a range of 1 to 15 MPa. The reaction temperature falls preferably in a range of 40 to 120° C. The reaction time depends on the reaction temperature and other conditions and can not indiscriminately be decided, and usually an extent of 30 to 360 minutes is enough.

Next, in the continuous flow system, the aromatic polycarboxylic acid is fed to a filling bed of the catalyst containing noble metal comprising rhodium or palladium or both of them at a velocity of 1 to 100 weight parts/hr per weight part of the noble metal described above, that is, a weight hour space velocity (WHSV) of 1 to 100 $h^{-1}$ to hydrogenate it at a hydrogen partial pressure of 1 MPa or more.

If the WHSV described above is less than 1 $h^{-1}$, the production efficiency is low and is not practical. If it exceeds 100 $h^{-1}$, the desired reaction conversion rate is not obtained, and the objects of the present invention shall not be achieved. The preferred WHSV falls in a range of 3 to 50 $h^{-1}$.

The hydrogen partial pressure and the reaction temperature are the same as described in the batch system described above. The continuous reactions of a liquid filling system and a liquid-through system are considered, and the liquid-through system is preferred.

In such batch system and continuous flow system, the catalyst used for the hydrogenation can repeatedly be used by subjecting it to activation treatment. Capable of being given as a method for the activation treatment of the catalyst are the methods of bringing into contact with air, treating with an oxidizing agent, bringing into contact with nitrogen gas, treating with steam and treating with an alkali aqueous solution. In the method of bringing into contact with air, the separated catalyst may merely be put in a vessel of glass and the like and left standing for several hours or more in the presence of air or the air may be forcibly passed through the catalyst bed by a method such as pressurized filtration or filtration under reduced pressure. Hydrogen peroxide is given as the example of the oxidizing agent. A sodium hydroxide aqueous solution and aqueous ammonia can be given as the example of the alkali. Preferably, when the catalyst is washed with the alkali, the catalyst is washed with aliphatic lower carboxylic acid such as acetic acid after washed with the alkali in order to reduce the residual alkali as much as possible and finally washed with water.

Among these activation treating methods, the method of bringing into contact with air, the method of treating with the oxidizing agent and a method of using them in combination are suited in terms of the activation effect.

An acid resistant material used for the hydrogen reaction apparatus includes corrosion resistant nickel alloys and molded articles thereof, super stainless steel and molded articles thereof, vitreous materials such as ceramic, porcelain enamel and glass and molded articles thereof. Capable of being given as the specific examples of the corrosion resistant nickel alloys are MAT 21 (manufactured by Mitsubishi Material Co., Ltd.), Hastelloy steels such as Hastelloy C-2000, Hastelloy C, Hastelloy C-276, Hastelloy C-22, Hastelloy B and Hastelloy B-2 (manufactured by Haynes International, Inc.) and Inconel steels such as Inconel 686 (manufactured by The International Nickel Company, Inc.). Capable of being given as the specific examples of the super stainless steel are NAS 254N and NAS 354N (manufactured by Nippon Yakin Ind. Co., Ltd.), Avesta 254SMO (manufactured by AVESTA Co., Ltd.) and HR8N and HR254 (manufactured by Sumitomo Metal Ind. Co., Ltd.).

Also, capable of being suitably used as well is a vessel in which the acid resistant material described above is lined on iron or stainless steel used for a conventional pressure proof vessel.

When water is used as the reaction solvent, the hydrogenated aromatic polycarboxylic acid which is the resulting product is dissolved in water which is the solvent, and therefore the filtrate is cooled or condensed, if necessary, after separating the noble metal to thereby precipitate the crystals of the hydrogenated aromatic polycarboxylic acid. This is subjected to solid-liquid separation, whereby the intended hydrogenated aromatic polycarboxylic acid can be obtained.

The hydrogenated aromatic polycarboxylic acid thus obtained may be a completely hydrogenated product or a partially hydrogenated product. When the raw material is, for example, a polycarboxylic acid having a naphthalene skeleton, a compound having a tetralin skeleton can be given as the partially hydrogenated product. Also, when the raw material is a polycarboxylic acid having a biphenyl skeleton or a skeleton of a structure in which two benzene rings are bonded via various linkage groups, a compound having a skeleton of a structure in which one is a benzene ring and the other is a cyclohexane ring can be given.

The hydrogenated aromatic polycarboxylic acid obtained by the process of the present invention can be converted into a hydrogenated aromatic polycarboxylic acid anhydride by further subjecting to dehydration reaction. The dehydration reaction can be carried out by heating and refluxing in the coexistence of a dehydrating agent such as acetic anhydride or by heating under reduced pressure.

Next, the process for producing the hydrogenated aromatic polycarboxylic acid anhydride shall be explained.

In the process for producing the hydrogenated aromatic polycarboxylic anhydride according to the present invention, the hydrogenated aromatic polycarboxylic acid having a high purity obtained by the process of the present invention (batch system or continuous flow system) is used as the hydrogenated aromatic polycarboxylic acid of the raw material. That is, used is (1) a compound obtained by hydrogenating the aromatic polycarboxylic acid at a hydrogen partial pressure of 1 MPa or more by a batch system in the presence of the catalyst containing noble metal comprising rhodium or palladium or both of them in a proportion of 0.5 to 10 parts by weight per 100 parts by weight of the aromatic polycarboxylic acid or (2) a compound obtained by feeding the aromatic polycarboxylic acid to a filling bed of the catalyst containing noble metal comprising rhodium or palladium or both of them at a velocity of 1 to 100 weight parts/hr per weight part of the noble metal described above to hydrogenate it at a hydrogen partial pressure of 1 MPa or more by a continuous flow system.

The kind of the raw material used in the process of the present invention shall not specifically be restricted, and it can suitably be selected according to the uses of the resulting acid anhydride from the completely hydrogenated products or the partially hydrogenated products of various aromatic polycarboxylic acids which have been given as the examples of the raw material in the descriptions of the process for producing the hydrogenated aromatic polycarboxylic acid described above.

Capable of being given as the preferred examples of this hydrogenated aromatic polycarboxylic acid are, for example, the completely hydrogenated products or the partially hydrogenated products of the aromatic polycarboxylic acids such as isophthalic acid, phthalic acid, 2,3-naphthalenedicarboxylic acid, anthracenedicarboxylic acid, trimellitic acid, 1,2,3-benzenetricarboxylic acid, trimesic acid, 1,2,4-naphthalenetricarboxylic acid, pyromellitic acid, 3,3',4,4'-benzophenonetetracarboxylic acid, 2,2',3,3'-benzophenonetetracarboxylic acid, 2,3,3',4'-benzophenonetetracarboxylic acid, 3,3',4,4'-biphenyltetracarboxylic acid, 2,2',3,3'-biphenyltetracarboxylic acid, 2,3,3',4'-biphenyltetracarboxylic acid, 4,4'-oxydiphthalic acid, diphenylmethanetetracarboxylic acid, 1,2,5,6-naphthalenetetracarboxylic acid, 2,3,6,7-naphthalenetetracarboxylic acid, 3,4,9,10-perylenetetracarboxylic acid, anthracene-tetracarboxylic acid, 4,4'-(hexafluoroisopropylidene) diphthalic acid, benzenepentacarboxylic acid and benzenehexacarboxylic acid.

The hydrogenated aromatic polycarboxylic acid of the raw material can be used either in a wet state (wet cake) in which it is subjected to solid-liquid separation after the hydrogenation reaction or in a crystalline state in which it is once dried by a dryer.

In the process of the present invention, the hydrogenated aromatic polycarboxylic acid described above is subjected to dehydration reaction with acetic anhydride of 0.64 to 5.7 times mole based on a carboxyl group of the hydrogenated aromatic polycarboxylic acid described above to thereby produce the hydrogenated aromatic polycarboxylic anhydride. In this case, a grade which is available in the market can be used for acetic anhydride as it is. If an amount of acetic anhydride is smaller than this range, the reaction rate is not sufficiently high. On the other hand, if it is larger than this range, it is difficult to recover the resulting hydrogenated aromatic polycarboxylic anhydride. Accordingly, both are not preferred.

The reaction temperature for advantageously carrying out the dehydration reaction is preferably 80 to 150° C. A suspension of the hydrogenated aromatic polycarboxylic acid and acetic anhydride may be only heated or acetic anhydride may be refluxed by heating. In the dehydration reaction, a slurry of the hydrogenated aromatic polycarboxylic acid suspended in acetic anhydride is heated while stirring, and when the dehydration temperature is reached, the state thereof is maintained for 1 to 60 minutes, whereby the dehydration reaction is completed.

This dehydration reaction is preferably carried out in inert gas atmosphere such as nitrogen gas.

In the present invention, glacial acetic acid is more preferably used as a solvent. An amount of glacial acetic acid used is preferably 0.5 to 10.0 times (weight ratio) as much as acetic anhydride. When a use amount of glacial acetic acid is increased, the dehydration reaction is carried out in a slurry state because of a small solubility of the hydrogenated aromatic polycarboxylic anhydride in glacial acetic acid. In this case, however, the dehydration reaction is completed as well, and therefore it does not matter.

Further, hydrocarbons, halogenated hydrocarbons, esters, ketones, ethers and aliphatic acids each having a boiling point of 50° C. or higher may be added as the second solvent.

After the dehydration reaction, the reaction liquid is cooled down to a room temperature to precipitate the crystal of the acid anhydride, and this is subjected to solid-liquid separation, whereby the hydrogenated aromatic polycarboxylic anhydride is obtained. When a mixed solvent of acetic anhydride and acetic acid is used, a precipitated amount of the crystal grows large, and therefore it is advantageous in terms of the process.

The mother liquid from which the crystal is separated may be circulated and reused. A proportion in which the mother liquid is sent back to the dehydration reactor can suitably be determined according to the degree of impurities accumulated in the system.

The hydrogenated aromatic polycarboxylic anhydride thus obtained may be an intermolecular acid anhydride or an acid anhydride having a cyclic acid anhydride group in a molecule. When it is used as a raw material for polyimide and an epoxy resin hardener, the acid anhydride having a cyclic acid anhydride group in a molecule is suited. A completely hydrogenated compound or a partially hydrogenated compound of an aromatic polycarboxylic acid having at least one pair of carboxyl groups which are bonded to an aromatic ring and adjacent to each other is used as the hydrogenated aromatic polycarboxylic acid of the raw material for producing such acid anhydride having a cyclic acid anhydride group in a molecule. For example, capable of being given as the representative example is a method in which used as the hydrogenated aromatic polycarboxylic acid of the raw material is 1,2,4,5-cyclohexanetetracarboxylic acid obtained by hydrogenating pyromellitic acid and in which this is subjected to cyclodehydration to obtain 1,2,4,5-cyclohexanetetracarboxylic dianhydride.

As described above, carrying out of the present invention makes it possible to produce the hydrogenated aromatic polycarboxylic anhydride having a high purity by a simple process and an industrially advantageous method.

According to the present invention, capable of being industrially advantageously produced at a good yield are the hydrogenated aromatic polycarboxylic acid and the acid anhydride thereof each having a high purity, which are used as a raw material for functional polyimides having properties such as transparency and solvent solubility and a curing agent for functional epoxy resins having transparency.

Next, the present invention shall be explained in further details with reference to examples, but the present invention shall by no means be restricted by these examples.

In the following examples, a noble metal catalyst amount (% by weight) shows parts by weight of the noble metal per 100 parts by weight of the aromatic polycarboxylic acid, and WHSV ($h^{-1}$) shows parts by weight/hr of the aromatic polycarboxylic acid per part by weight of the noble metal.

EXAMPLE 1

An autoclave (equipped with a stirrer) of 5 liters made of Hastelloy C-22 was charged with 276 g of pyromellitic acid, 1656 g of water and 100 g of a 5 weight % Rh-carbon powder catalyst (hydrous product, moisture content: 50.5% by weight, manufactured by N. E. CHEMCAT Co., Ltd.), and it was substituted in a system twice with nitrogen gas and then three times with hydrogen gas while stirring. The temperature was elevated while maintaining the hydrogen pressure at 4.9 MPa to carry out hydrogenation reaction at a reaction temperature of 60° C. for 60 minutes. The reaction liquid was taken out from the autoclave, and the 5 weight % Rh-carbon powder catalyst was filtered and separated by means of a vacuum filtering equipment (filter: 5B filter paper) to obtain a colorless and transparent filtrate.

This filtrate was analyzed by gas chromatography to find that a conversion rate of pyromellitic acid was 99.92% and a selectivity of 1,2,4,5-cyclohexanetetracarboxylic acid was 98.3% (Rh catalyst amount: 0.90% by weight, reaction yield: 98.2%).

The filtrate was condensed under reduced pressure by means of a rotary evaporator to precipitate the crystal of 1,2,4,5-cyclohexane-tetracarboxylic acid. This crystal was separated and dried to obtain 263 g of 1,2,4,5-cyclohexane-tetracarboxylic acid crystal. This crystal was analyzed by gas chromatography to result in finding that 1,2,4,5-cyclohexanetetracarboxylic acid had a purity of 99.0%.

EXAMPLE 2

The same autoclave as used in Example 1 was charged with 414 g of pyromellitic acid, 1656 g of water and 150 g of the 5 weight % Rh-carbon powder catalyst (described above), and it was substituted in a system twice with nitrogen gas and then three times with hydrogen gas while stirring. The temperature was elevated while maintaining the hydrogen pressure at 5.1 MPa to carry out hydrogenation reaction at a reaction temperature of 70° C. for 120 minutes.

The reaction liquid was taken out from the autoclave, and the 5 weight % Rh-carbon powder catalyst was filtered and separated by means of the vacuum filtering equipment (filter: 5B filter paper) to obtain a colorless and transparent filtrate.

This filtrate was analyzed by gas chromatography to find that a conversion rate of pyromellitic acid was 99.90% and a selectivity of 1,2,4,5-cyclohexanetetracarboxylic acid was 98.6% (Rh catalyst amount: 0.90% by weight, reaction yield: 98.5%).

The filtrate was condensed under reduced pressure by means of a rotary evaporator to precipitate the crystal of 1,2,4,5-cyclohexane-tetracarboxylic acid. This crystal was separated and dried to obtain 385 g of 1,2,4,5-cyclohexane-tetracarboxylic acid crystal. This crystal was analyzed by gas chromatography to result in finding that 1,2,4,5-cyclohexanetetracarboxylic acid had a purity of 98.7%.

EXAMPLE 3

The same autoclave as used in Example 1 was charged with 828 g of pyromellitic acid, 1656 g of water and 200 g of the 5 weight % Rh-carbon powder catalyst (described above), and it was substituted in a system twice with nitrogen gas and then three times with hydrogen gas while stirring. The temperature was elevated while maintaining the hydrogen pressure at 5.0 MPa to carry out hydrogenation reaction at a reaction temperature of 80° C. for 120 minutes.

The reaction liquid was taken out from the autoclave, and the 5 weight % Rh-carbon powder catalyst was filtered and separated by means of the vacuum filtering equipment (filter: 5B filter paper) to obtain a colorless and transparent filtrate.

This filtrate was analyzed by gas chromatography to find that a conversion rate of pyromellitic acid was 99.89% and a selectivity of 1,2,4,5-cyclohexanetetracarboxylic acid was 97.7% (Rh catalyst amount: 0.60% by weight, reaction yield: 97.6%).

The filtrate was condensed under reduced pressure by means of a rotary evaporator to precipitate the crystal of 1,2,4,5-cyclohexane-tetracarboxylic acid. This crystal was separated and dried to obtain 781 g of 1,2,4,5-cyclohexane-tetracarboxylic acid crystal. This crystal was analyzed by gas chromatography to result in finding that 1,2,4,5-cyclohexanetetracarboxylic acid had a purity of 98.5%.

EXAMPLE 4

The same autoclave as used in Example 1 was charged with 276 g of pyromellitic acid, 1656 g of water and 100 g of the 5 weight % Rh-carbon powder catalyst (described above), and it was substituted in a system twice with nitrogen gas and then three times with hydrogen gas while stirring. The temperature was elevated while maintaining the hydrogen pressure at 3.1 MPa to carry out hydrogenation reaction at a reaction temperature of 80° C. for 360 minutes.

The reaction liquid was taken out from the autoclave, and the 5 weight % Rh-carbon powder catalyst was filtered and separated by means of the vacuum filtering equipment (filter: 5B filter paper) to obtain a colorless and transparent filtrate.

This filtrate was analyzed by gas chromatography to find that a conversion rate of pyromellitic acid was 99.86% and a selectivity of 1,2,4,5-cyclohexanetetracarboxylic acid was 97.9% (Rh catalyst amount: 0.90% by weight, reaction yield: 97.8%).

The filtrate was condensed under reduced pressure by means of a rotary evaporator to precipitate the crystal of 1,2,4,5-cyclohexane-tetracarboxylic acid. This crystal was separated and dried to obtain 249 g of 1,2,4,5-cyclohexane-tetracarboxylic acid crystal. This crystal was analyzed by gas chromatography to result in finding that 1,2,4,5-cyclohexanetetracarboxylic acid had a purity of 98.2%.

EXAMPLE 5

The same autoclave as used in Example 1 was charged with 276 g of pyromellitic acid, 1656 g of water and 100 g of the 5 weight % Rh-carbon powder catalyst (described above), and it was substituted in a system twice with nitrogen gas and then three times with hydrogen gas while stirring. The temperature was elevated while maintaining the hydrogen pressure at 6.8 MPa to carry out hydrogenation reaction at a reaction temperature of 50° C. for 60 minutes.

The reaction liquid was taken out from the autoclave, and the 5 weight % Rh-carbon powder catalyst was filtered and separated by means of the vacuum filtering equipment (filter: 5B filter paper) to obtain a colorless and transparent filtrate.

This filtrate was analyzed by gas chromatography to find that a conversion rate of pyromellitic acid was 99.94% and a selectivity of 1,2,4,5-cyclohexanetetracarboxylic acid was 98.1% (Rh catalyst amount: 0.90% by weight, reaction yield: 98.0%).

The filtrate was condensed under reduced pressure by means of a rotary evaporator to precipitate the crystal of 1,2,4,5-cyclohexane-tetracarboxylic acid. This crystal was separated and dried to obtain 262 g of 1,2,4,5-cyclohexane-tetracarboxylic acid crystal. This crystal was analyzed by gas chromatography to result in finding that 1,2,4,5-cyclohexanetetracarboxylic acid had a purity of 99.1%.

COMPARATIVE EXAMPLE 1

An autoclave (equipped with a stirrer) of 5 liters made of Hastelloy C-22 was charged with 276 g of pyromellitic acid, 1656 g of water and 12 g of a 5 weight % Rh-carbon powder catalyst (hydrous product, moisture content: 51.5% by weight, manufactured by N. E. CHEMCAT Co., Ltd.), and it was substituted in a system twice with nitrogen gas and then three times with hydrogen gas while stirring. The temperature was elevated while maintaining the hydrogen pressure at 5.0 MPa to carry out hydrogenation reaction at a reaction temperature of 80° C. for 240 minutes.

The reaction liquid was taken out from the autoclave, and the 5 weight % Rh-carbon powder catalyst was filtered and separated by means of the vacuum filtering equipment (filter: 5B filter paper) to obtain a brown and transparent filtrate.

This filtrate was analyzed by gas chromatography to find that a conversion rate of pyromellitic acid was 18.0% and a selectivity of 1,2,4,5-cyclohexanetetracarboxylic acid was 75.6% (Rh catalyst amount: 0.11% by weight, reaction yield: 13.6%).

COMPARATIVE EXAMPLE 2

The autoclave (equipped with a stirrer) of 5 liters made of Hastelloy C-22 was charged with 276 g of pyromellitic acid, 1656 g of water and 12 g of the 5 weight % Rh-carbon powder catalyst (hydrous product, moisture content: 51.5% by weight, manufactured by N. E. CHEMCAT Co., Ltd.), and it was substituted in a system twice with nitrogen gas and then three times with hydrogen gas while stirring. The temperature was elevated while maintaining the hydrogen pressure at 7.0 MPa to carry out hydrogenation reaction at a reaction temperature of 120° C. for 180 minutes.

The reaction liquid was taken out from the autoclave, and the 5 weight % Rh-carbon powder catalyst was filtered and separated by means of the vacuum filtering equipment (filter: 5B filter paper) to obtain a brown and transparent filtrate.

This filtrate was analyzed by gas chromatography to find that a conversion rate of pyromellitic acid was 27.7% and a selectivity of 1,2,4,5-cyclohexanetetracarboxylic acid was 82.5% (Rh catalyst amount: 0.11% by weight, reaction yield: 22.9%)

COMPARATIVE EXAMPLE 3

An autoclave (equipped with a stirrer) of 18 liters made of Hastelloy C-276 was charged with 2.5 kg of pyromellitic acid, 10 kg of water and 1.2 kg of a 5 weight % Ru-carbon powder catalyst (hydrous product, moisture content: 50.4% by weight, manufactured by N. E. CHEMCAT Co., Ltd.), and it was substituted in a system three times with nitrogen gas while stirring. Hydrogen was introduced thereinto, and the temperature was elevated while maintaining the hydrogen pressure at 4.0 MPa to carry out hydrogenation reaction at a reaction temperature of 70° C. for 120 minutes.

The reaction liquid was taken out from the autoclave, and the 5 weight % Ru-carbon powder catalyst was filtered and separated by means of the vacuum filtering equipment (filter: 5B filter paper) to obtain a brown and transparent filtrate.

This filtrate was analyzed by gas chromatography to find that a conversion rate of pyromellitic acid was 91.0% and a selectivity of 1,2,4,5-cyclohexanetetracarboxylic acid was 56.8% (Ru catalyst amount: 1.2% by weight, reaction yield: 51.7%).

COMPARATIVE EXAMPLE 4

The autoclave (equipped with a stirrer) of 18 liters made of Hastelloy C-276 was charged with 2.5 kg of pyromellitic acid, 10 kg of water and 1.2 kg of a 5 weight % Rh-carbon powder catalyst (hydrous product, moisture content: 50.5% by weight, manufactured by N. E. CHEMCAT Co., Ltd.), and it was substituted in a system three times with nitrogen gas while stirring. Hydrogen was introduced thereinto, and the temperature was elevated while maintaining the hydrogen pressure at 0.3 MPa to carry out hydrogenation reaction at a reaction temperature of 70° C. for 120 minutes.

The reaction liquid was taken out from the autoclave, and the 5 weight % Rh-carbon powder catalyst was filtered and separated by means of the vacuum filtering equipment (filter: 5B filter paper) to obtain a colorless and transparent filtrate.

This filtrate was analyzed by gas chromatography to find that a conversion rate of pyromellitic acid was 69.2% and a selectivity of 1,2,4,5-cyclohexanetetracarboxylic acid was 91.3% (Rh catalyst amount: 1.2% by weight, reaction yield: 63.2%).

EXAMPLE 6

A reaction tube (inner diameter 16 mm×length 320 mm) made of Hastelloy C-22 was charged with 10 g of a 0.5 weight % Rh-carbon granule catalyst (manufactured by N. E. CHEMCAT Co., Ltd.) at the upper and lower parts of a catalyst bed using Raschig rings. A pyromellitic acid aqueous solution of 15% by weight was prepared and charged into a raw material mixing bath, and it was heated to 80° C. while stirring. The inside of the raw material mixing bath was placed in nitrogen atmosphere. This pyromellitic acid aqueous solution was fed into the reaction tube maintained at a reaction pressure of 12 MPa with hydrogen gas in a proportion of 5.0 g/hr by means of a pump to continuously carry out hydrogenation reaction on the fixed bed. Hydrogen consumed in the reaction was fed from the upper part of the reaction tube so that the reaction pressure was maintained. The reaction tube was heated to carry out the reaction at 100° C. The reaction liquid falling down through the reaction tube was stored in a product-receiving bath connected to the lower part of the reaction tube and intermittently drawn out from a liquid phase part at the lower part thereof. In this case, the reaction gas was slightly drawn out from the gas phase part of the product-receiving bath (WHSV: 15 $hr^{-1}$).

The reaction liquid drawn out after 6 to 7 hours since starting the reaction was analyzed by gas chromatography to find that a conversion rate of pyromellitic acid was 99.85% and a selectivity of 1,2,4,5-cyclohexanetetracarboxylic acid was 95.8% (reaction yield: 95.7%).

EXAMPLE 7

The reaction tube (inner diameter 16 mm×length 320 mm) made of Hastelloy C-22 was charged with 5 g of a 2 weight % Rh-carbon granule catalyst (manufactured by N. E. CHEMCAT Co., Ltd.) at the upper and lower parts of a catalyst bed using Raschig rings. A pyromellitic acid aqueous solution of 15% by weight was prepared and charged into a raw material mixing bath, and it was heated to 80° C. while stirring. The inside of the raw material mixing bath was placed in nitrogen atmosphere. This pyromellitic acid aqueous solution was fed into the reaction tube maintained at a reaction pressure of 10 MPa with hydrogen gas in a proportion of 7.5 g/hr by means of a pump to continuously carry out hydrogenation reaction on the fixed bed. Hydrogen consumed in the reaction was fed from the upper part of the reaction tube so that the reaction pressure was maintained. The reaction tube was heated to carry out the reaction at 90° C. The reaction liquid falling down through the reaction tube was stored in a product-receiving bath connected to the lower part of the reaction tube and intermittently drawn out from a liquid phase part at the lower part thereof. In this case, the reaction gas was slightly drawn out from the gas phase part of the product-receiving bath (WHSV: 11.3 $hr^{-1}$).

The reaction liquid drawn out after 6 to 7 hours since starting the reaction was analyzed by gas chromatography to find that a conversion rate of pyromellitic acid was 99.88% and a selectivity of 1,2,4,5-cyclohexanetetracarboxylic acid was 95.5% (reaction yield: 95.4%).

EXAMPLE 8

The autoclave (equipped with a stirrer) of 18 liters made of Hastelloy C-276 was charged with 2.5 kg of pyromellitic acid, 10 kg of water and 1.2 kg of a 5 weight % Rh-carbon powder catalyst (hydrous product, moisture content: 50.5% by weight, manufactured by N. E. CHEMCAT Co., Ltd.), and it was substituted in a system three times with nitrogen gas while stirring. Hydrogen was introduced thereinto, and the temperature was elevated while maintaining the hydrogen pressure at 4.0 MPa to carry out hydrogenation reaction at a reaction temperature of 70° C. for 120 minutes.

The reaction liquid was taken out from the autoclave, and the 5 weight % Rh-carbon powder catalyst was filtered and separated by means of the vacuum filtering equipment (filter: 5B filter paper) to obtain a colorless and transparent filtrate.

This filtrate was analyzed by gas chromatography to find that a conversion rate of pyromellitic acid was 99.94% and a selectivity of 1,2,4,5-cyclohexanetetracarboxylic acid was 94.8% (Rh catalyst amount: 1.2% by weight, reaction yield: 94.7%).

The filtrate was condensed under reduced pressure by means of a rotary evaporator to precipitate the crystal of 1,2,4,5-cyclohexane-tetracarboxylic acid. This crystal was separated and dried to obtain 2.2 kg of 1,2,4,5-cyclohexane-tetracarboxylic acid crystal. This crystal was analyzed by gas chromatography to result in finding that 1,2,4,5-cyclohexanetetracarboxylic acid had a purity of 99.0%.

EXAMPLE 9

The hydrogenation reaction was carried out in the same manner as in Example 8, except that the 5 weight % Rh-carbon powder catalyst used in Example 8 was separated by filtration under reduced pressure and then put on a glass-made vessel to leave it standing in the air for a night, and then it was used.

The reaction liquid was taken out from the autoclave, and the 5 weight % Rh-carbon powder catalyst was filtered and separated by means of the vacuum filtering equipment (filter: 5B filter paper) to obtain a colorless and transparent filtrate.

This filtrate was analyzed by gas chromatography to find that a conversion rate of pyromellitic acid was 99.94% and a selectivity of 1,2,4,5-cyclohexanetetracarboxylic acid was 94.8% (Rh catalyst amount: 1.2% by weight, reaction yield: 94.7%).

The filtrate was condensed under reduced pressure by means of a rotary evaporator to precipitate the crystal of 1,2,4,5-cyclohexane-tetracarboxylic acid. This crystal was separated and dried to obtain 2.2 kg of 1,2,4,5-cyclohexane-tetracarboxylic acid crystal. This crystal was analyzed by gas chromatography to result in finding that 1,2,4,5-cyclohexanetetracarboxylic acid had a purity of 98.7%.

Also, the 5 weight % Rh-carbon powder catalyst used on the same reaction conditions as in Example 8 was separated by filtration under reduced pressure and then immediately charged into the autoclave (equipped with a stirrer) of 18 liters made of Hastelloy C-276 together with 2.5 kg of pyromellitic acid and 10 kg of water to carry out hydrogenation reaction in the same manner as in Example 8.

The reaction liquid was taken out from the autoclave, and the 5 weight % Rh-carbon powder catalyst was filtered and separated by means of the vacuum filtering equipment (filter: 5B filter paper) to obtain a brown and transparent filtrate.

This filtrate was analyzed by gas chromatography to find that a conversion rate of pyromellitic acid was 54.0% and a selectivity of 1,2,4,5-cyclohexanetetracarboxylic acid was 92.1% (reaction yield: 49.7%).

Thus, it can be found that when the catalyst is immediately used for the subsequent reaction without carrying out activation treatment of leaving the used catalyst standing in the air, the reaction conversion rate is notably reduced due to a reduction in the catalyst activity.

EXAMPLES 10 TO 17

Carried out were recycle experiments in which the catalyst used in the preceding experiment was left standing in the air in the same manner as in Example 9 to carry out activation treatment and repeatedly used. The results thereof are summarized in Table 1. A reduction in the catalyst activity was not observed.

TABLE 1

|  | Conversion rate (%) | Selectivity (%) | Recycle number |
|---|---|---|---|
| Example 9 | 99.94 | 94.8 | First |
| Example 10 | 99.96 | 95.0 | Second |
| Example 11 | 99.94 | 94.7 | Third |
| Example 12 | 99.97 | 94.9 | Fourth |
| Example 13 | 99.97 | 94.3 | Fifth |
| Example 14 | 99.95 | 93.9 | Sixth |
| Example 15 | 99.94 | 94.1 | Seventh |
| Example 16 | 99.93 | 94.3 | Eighth |
| Example 17 | 99.98 | 94.3 | Ninth |

EXAMPLE 18

The autoclave (equipped with a stirrer) of 18 liters made of Hastelloy C-276 was charged with 1.8 kg of trimellitic acid, 10.8 kg of water and 1.2 kg of a 5 weight % Rh-carbon powder catalyst (hydrous product, moisture content: 50.5% by weight, manufactured by N. E. CHEMCAT Co., Ltd.), and it was substituted in a system three times with nitrogen gas while stirring. Hydrogen was introduced thereinto, and the temperature was elevated while maintaining the hydrogen pressure at 3.0 MPa to carry out hydrogenation reaction at a reaction temperature of 70° C. for 60 minutes.

The reaction liquid was taken out from the autoclave, and the 5 weight % Rh-carbon powder catalyst was filtered and separated by means of the vacuum filtering equipment (filter: 5B filter paper) to obtain a colorless and transparent filtrate.

This filtrate was analyzed by gas chromatography to find that a conversion rate of trimellitic acid was 99.94% and a selectivity of 1,2,4-cyclohexanetricarboxylic acid was 94.7% (Rh catalyst amount: 1.7% by weight, reaction yield: 94.6%).

The filtrate was condensed under reduced pressure by means of a rotary evaporator to precipitate the crystal of 1,2,4-cyclohexane-tricarboxylic acid. This crystal was separated and dried to obtain 1.2 kg of 1,2,4-cyclohexane-tricarboxylic acid crystal. This crystal was analyzed by gas chromatography to result in finding that 1,2,4-cyclohexanetricarboxylic acid had a purity of 98.6%.

EXAMPLE 19

The hydrogenation reaction was carried out in the same manner as in Example 18, except that the 5 weight % Rh-carbon powder catalyst used in Example 18 was separated by filtration under reduced pressure and then put on a glass-made vessel to leave it standing in the air for a night, and then it was used.

The reaction liquid was taken out from the autoclave, and the 5 weight % Rh-carbon powder catalyst was filtered and separated by means of the vacuum filtering equipment (filter: 5B filter paper) to obtain a brown and transparent filtrate.

This filtrate was analyzed by gas chromatography to find that a conversion rate of trimellitic acid was 99.95% and a selectivity of 1,2,4-cyclohexanettricarboxylic acid was 94.6% (reaction yield: 94.6%).

Also, the 5 weight % Rh-carbon powder catalyst used on the same reaction conditions as in Example 18 was separated by filtration under reduced pressure and then immediately charged into the autoclave (equipped with a stirrer) of 18 liters made of Hastelloy C-276 together with 1.8 kg of trimellitic acid and 10.8 kg of water to carry out hydrogenation reaction in the same manner as in Example 18.

The reaction liquid was taken out from the autoclave, and the 5 weight % Rh-carbon powder catalyst was filtered and separated by means of the vacuum filtering equipment (filter: 5B filter paper) to obtain a brown filtrate.

This filtrate was analyzed by gas chromatography to find that a conversion rate of pyromellitic acid was 59.2% and a selectivity of 1,2,4-cyclohexanetricarboxylic acid was 89.9% (Rh catalyst amount: 1.7% by weight, reaction yield: 53.2%).

Thus, it can be found that when the catalyst is immediately used for the subsequent reaction without carrying out activation treatment of leaving the used catalyst standing in the air, the reaction conversion rate is notably reduced due to a reduction in the catalyst activity.

EXAMPLES 20 TO 27

Carried out were recycle experiments in which the catalyst used in the preceding experiment was left standing in the air to carry out activation treatment and repeatedly used. The results thereof are summarized in Table 2. A reduction in the catalyst activity was not observed.

TABLE 2

|  | Conversion rate (%) | Selectivity (%) | Recycle number |
|---|---|---|---|
| Example 19 | 99.95 | 94.6 | First |
| Example 20 | 99.96 | 93.9 | Second |
| Example 21 | 99.95 | 94.1 | Third |
| Example 22 | 99.94 | 94.2 | Fourth |

TABLE 2-continued

|  | Conversion rate (%) | Selectivity (%) | Recycle number |
|---|---|---|---|
| Example 23 | 99.94 | 94.0 | Fifth |
| Example 24 | 99.95 | 93.9 | Sixth |
| Example 25 | 99.93 | 94.1 | Seventh |
| Example 26 | 99.95 | 93.8 | Eighth |
| Example 27 | 99.94 | 93.8 | Ninth |

EXAMPLE 28

The hydrogenation reaction was carried out in the same manner as in Example 18, except that trimesic acid was substituted for trimellitic acid.

The reaction liquid was taken out from the autoclave, and the 5 weight % Rh-carbon powder catalyst was filtered and separated by means of the vacuum filtering equipment (filter: 5B filter paper) to obtain a colorless and transparent filtrate.

This filtrate was analyzed by gas chromatography to find that a conversion rate of trimesic acid was 100.0% and a selectivity of 1,3,5-cyclohexanetricarboxylic acid was 97.5% (Rh catalyst amount: 1.7% by weight, reaction yield: 97.5%)

The filtrate was condensed under reduced pressure by means of a rotary evaporator to precipitate the crystal of 1,3,5-cyclohexane-tricarboxylic acid. This crystal was separated and dried to obtain 1.2 kg of 1,3,5-cyclohexane-tricarboxylic acid crystal. This crystal was analyzed by gas chromatography to result in finding that 1,2,4-cyclohexanetricarboxylic acid had a purity of 98.9%.

EXAMPLE 29

The hydrogenation reaction was carried out in the same manner as in Example 28, except that 1.8 kg of a 5 weight % Pd-carbon powder catalyst (hydrous product, moisture content: 54.4% by weight, manufactured by N. E. CHEMCAT Co., Ltd.) was substituted for 1.2 kg of the 5 weight % Rh-carbon powder catalyst The reaction liquid was taken out from the autoclave, and the 5 weight % Pd-carbon powder catalyst was filtered and separated by means of the vacuum filtering equipment (filter: 5B filter paper) to obtain a colorless and transparent filtrate.

This filtrate was analyzed by gas chromatography to find that a conversion rate of trimesic acid was 99.96% and a selectivity of 1,3,5-cyclohexanetricarboxylic acid was 97.1% (Pd catalyst amount: 2.3% by weight, reaction yield: 97.1%).

The filtrate was condensed under reduced pressure by means of a rotary evaporator to precipitate the crystal of 1,3,5-cyclohexane-tricarboxylic acid. This crystal was separated and dried to obtain 1.2 kg of 1,3,5-cyclohexane-tricarboxylic acid crystal. This crystal was analyzed by gas chromatography to result in finding that 1,2,4-cyclohexanetricarboxylic acid had a purity of 98.8%.

EXAMPLE 30

A reaction tube (inner diameter 30 mm×length 500 mm) made of Hastelloy C-22 was charged with 100 g of the 2 weight % Rh-carbon granule catalyst (manufactured by N. E. CHEMCAT Co., Ltd.) at the upper and lower parts of a catalyst bed using Raschig rings. A trimellitic acid aqueous solution of 9.1% by weight was prepared and charged into a raw material mixing bath, and it was heated to 80° C. while stirring. The inside of the raw material mixing bath was placed in nitrogen atmosphere. This trimellitic acid aqueous solution was fed into the reaction tube maintained at a reaction pressure of 8.0 MPa with hydrogen gas in a proportion of 200 g/hr by means of a pump to continuously carry out hydrogenation reaction on the fixed bed. Hydrogen consumed in the reaction was fed from the upper part of the reaction tube so that the reaction pressure was maintained. The reaction tube was heated to carry out the reaction at 90° C. The reaction liquid falling down through the reaction tube was stored in a product-receiving bath connected to the lower part of the reaction tube and intermittently drawn out from a liquid phase part at the lower part thereof. In this case, the reaction gas was slightly drawn out from the gas phase part of the product-receiving bath (WHSV: 9.1 hr$^{-1}$).

The reaction liquid drawn out after 9 to 10 hours since starting the reaction was analyzed by gas chromatography to find that a conversion rate of trimellitic acid was 99.95% and a selectivity of 1,2,4-cyclohexanetricarboxylic acid was 94.2% (reaction yield: 94.2%).

EXAMPLE 31

A reaction tube (inner diameter 30 mm×length 500 mm) made of Hastelloy C-22 was charged with 100 g of the 2 weight % Rh-carbon granule catalyst (manufactured by N. E. CHEMCAT Co., Ltd.) at the upper and lower parts of a catalyst bed using Raschig rings. A trimellitic acid aqueous solution of 9.1% by weight was prepared and charged into a raw material mixing bath, and it was heated to 80° C. while stirring. The inside of the raw material mixing bath was placed in nitrogen atmosphere. This trimellitic acid aqueous solution was fed into the reaction tube maintained at a reaction pressure of 4.0 MPa with hydrogen gas in a proportion of 200 g/hr by means of a pump to continuously carry out hydrogenation reaction on the fixed bed. Hydrogen consumed in the reaction was fed from the upper part of the reaction tube so that the reaction pressure was maintained. The reaction tube was heated to carry out the reaction at 90° C. The reaction liquid falling down through the reaction tube was stored in a product-receiving bath connected to the lower part of the reaction tube and intermittently drawn out from a liquid phase part at the lower part thereof. In this case, the reaction gas was slightly drawn out from the gas phase part of the product-receiving bath (WHSV: 9.1 hr$^{-1}$).

The reaction liquid drawn out after 4 to 5 hours since starting the reaction was analyzed by gas chromatography to find that a conversion rate of trimellitic acid was 99.92% and a selectivity of 1,2,4-cyclohexanetricarboxylic acid was 94.4% (reaction yield: 94.3%).

EXAMPLE 32

A flask of 3 liters equipped with a Dimroth condenser and a stirrer was charged with 200 g of 1,2,4,5-cyclohexanetetracarboxylic acid obtained in the same manner as in Example 1 and 800 g (2.5 times mole based on a carboxyl group) of acetic anhydride and substituted in a system with nitrogen gas while stirring. The temperature was elevated while allowing a trace amount of nitrogen gas to flow to carry out refluxing for 30 minutes.

The reaction liquid was cooled down to a room temperature to precipitate crystal, and the crystal was separated (rinsed with 50 g of acetic anhydride) and dried to obtain 143 g of 1,2,4,5-cyclohexane-tetracarboxylic anhydride. Analysis of this crystal resulted in showing that 1,2,4,5- cyclohexane-tetracarboxylic anhydride had a purity of 99.4%. Also, a yield of 1,2,4,5-cyclohexanetetracarboxylic anhydride was 83.0%.

The product (crystal) was analyzed by gas chromatography and liquid chromatography (hereinafter the same shall apply).

EXAMPLE 33

The same flask as used in Example 32 was charged with 200 g of 1,2,4,5-cyclohexane-tetracarboxylic acid obtained in the same manner as in Example 6 and 800 g (2.5 times mole based on a carboxyl group) of acetic anhydride and substituted in a system with nitrogen gas while stirring. The temperature was elevated while allowing a trace amount of nitrogen gas to flow to carry out refluxing for 5 minutes.

The reaction liquid was cooled down to a room temperature to precipitate crystal, and the crystal was separated (rinsed with 50 g of acetic anhydride) and dried to obtain 146 g of 1,2,4,5-cyclohexane-tetracarboxylic anhydride. Analysis of this crystal resulted in showing that 1,2,4,5-cyclohexane-tetracarboxylic anhydride had a purity of 99.3%. Also, a yield of 1,2,4,5-cyclohexanetetracarboxylic anhydride was 84.7%.

EXAMPLE 34

The same flask as used in Example 32 was charged with 200 g of 1,2,4,5-cyclohexane-tetracarboxylic acid obtained in the same manner as in Example 1, 300 g (1.0 times mole based on a carboxyl group) of acetic anhydride and 1500 g of glacial acetic acid and substituted in a system with nitrogen gas while stirring. The temperature was elevated while allowing a trace amount of nitrogen gas to flow to carry out refluxing for 5 minutes.

The reaction liquid was cooled down to a room temperature to precipitate crystal, and the crystal was separated (rinsed with 50 g of acetic anhydride) and dried to obtain 161 g of 1,2,4,5-cyclohexane-tetracarboxylic anhydride. Analysis of this crystal resulted in showing that 1,2,4,5-cyclohexane-tetracarboxylic anhydride had a purity of 99.1%. Also, a yield of 1,2,4,5-cyclohexanetetracarboxylic anhydride was 93.4%.

EXAMPLE 35

The same flask as used in Example 32 was charged with 200 g of 1,2,4,5-cyclohexane-tetracarboxylic acid obtained in the same manner as in Example 1 and 1880 g of the separated mother liquid obtained in Example 32 and substituted in a system with nitrogen gas while stirring. The temperature was elevated while allowing a trace amount of nitrogen gas to flow to carry out refluxing for 5 minutes.

The reaction liquid was cooled down to a room temperature to precipitate crystal, and the crystal was separated (rinsed with 50 g of acetic anhydride) and dried to obtain 170 g of 1,2,4,5-cyclohexane-tetracarboxylic anhydride. Analysis of this crystal resulted in showing that 1,2,4,5-cyclohexane-tetracarboxylic anhydride had a purity of 99.0%. Also, a yield (based on 1,2,4,5-cyclohexanetetracarboxylic acid of the raw material) of 1,2,4,5-cyclohexanetetracarboxylic anhydride was 92.6%.

COMPARATIVE EXAMPLE 5

The same flask as used in Example 32 was charged with 200 g of 1,2,4,5-cyclohexane-tetracarboxylic acid obtained in the same manner as in Example 1 and 2000 g (6.4 times mole based on a carboxyl group) of acetic anhydride and substituted in a system with nitrogen gas while stirring. The temperature was elevated while allowing a trace amount of nitrogen gas to flow to carry out refluxing for 30 minutes.

The reaction liquid was cooled down to a room temperature to precipitate crystal, and the crystal was separated (rinsed with 50 g of acetic anhydride) and dried to obtain 103 g of 1,2,4,5-cyclohexane-tetracarboxylic anhydride. Analysis of this crystal resulted in showing that 1,2,4,5-cyclohexane-tetracarboxylic anhydride had a purity of 99.5%. Also, a yield of 1,2,4,5-cyclohexanetetracarboxylic anhydride was 59.8%.

What is claimed is:

1. A process for producing a hydrogenated aromatic polycarboxylic acid, wherein in hydrogenating an aromatic polycarboxylic acid by a batch system, the aromatic polycarboxylic acid is hydrogenated at a hydrogen partial pressure of 1 MPa or more in the presence of a catalyst containing noble metal comprising rhodium or palladium or both of them in a proportion of 0.5 to 10 parts by weight per 100 parts by weight of the aromatic polycarboxylic acid and wherein the catalyst used for the hydrogenation is thereafter subjected to activation treatment with at least one of air and an oxidizing agent and reused.

2. The process for producing a hydrogenated aromatic polycarboxylic acid as described in claim 1, wherein a hydrogenating temperature is 40 to 120° C.

3. The process for producing a hydrogenated aromatic polycarboxylic acid as described in claim 1, wherein the hydrogen partial pressure is 1 to 15 MPa.

4. The process for producing a hydrogenated aromatic polycarboxylic acid as described in claim 1, wherein the aromatic polycarboxylic acid dissolved or dispersed in a solvent is used.

5. The process for producing a hydrogenated aromatic polycarboxylic acid as described in claim 4, wherein the aromatic polycarboxylic acid contained in the solution comprising the aromatic polycarboxylic acid and the solvent has a concentration of 5 to 50% by weight.

6. The process for producing a hydrogenated aromatic polycarboxylic acid as described in claim 1, wherein the aromatic polycarboxylic acid is pyromellitic acid, trimellitic acid or trimesic acid.

7. A process for producing a hydrogenated aromatic polycarboxylic acid, wherein in hydrogenating an aromatic polycarboxylic acid by a continuous flow system, the aromatic polycarboxylic acid is fed to a filling bed of a catalyst containing noble metal comprising rhodium or palladium or both of them at a velocity of 1 to 100 weight parts/hr per weight part of the noble metal described above to hydrogenate it at a hydrogen partial pressure of 1 MPa or more, and wherein the catalyst used for the hydrogenation is thereafter subjected to activation treatment with at least one of air and an oxidizing agent and reused.

8. The process for producing a hydrogenated aromatic polycarboxylic acid as described in claim 7, wherein a hydrogenating temperature is 40 to 120° C.

9. The process for producing a hydrogenated aromatic polycarboxylic acid as described in claim 7, wherein the hydrogen partial pressure is 1 to 15 MPa.

10. The process for producing a hydrogenated aromatic polycarboxylic acid as described in claim 7, wherein the aromatic polycarboxylic acid dissolved or dispersed in a solvent is used.

11. The process for producing a hydrogenated aromatic polycarboxylic acid as described in claim 10, wherein the aromatic polycarboxylic acid contained in the solution comprising the aromatic polycarboxylic acid and the solvent has a concentration of 5 to 50% by weight.

12. The process for producing a hydrogenated aromatic polycarboxylic acid as described in claim 7, wherein the aromatic polycarboxylic acid is pyromellitic acid, trimellitic acid or trimesic acid.

13. A process for producing a hydrogenated aromatic polycarboxylic anhydride, wherein in producing an acid anhydride by dehydration reaction of a hydrogenated aromatic polycarboxylic acid, used as the above hydrogenated aromatic polycarboxylic acid is one obtained by hydrogenating an aromatic polycarboxylic acid at a hydrogen partial pressure of 1 MPa or more by a batch system in the presence of a catalyst containing noble metal comprising rhodium or palladium or both of them in a proportion of 0.5 to 10 parts by weight per 100 parts by weight of the aromatic polycarboxylic acid; and the above hydrogenated aromatic polycarboxylic acid is subjected to dehydration reaction with acetic anhydride of 0.64 to 5.7 times mole based on a carboxyl group of the hydrogenated aromatic polycarboxylic acid, the dehydration reaction being carried out in a glacial acetic acid solvent.

14. The process for producing a hydrogenated aromatic polycarboxylic anhydride as described in claim 13, wherein an amount of the glacial acetic acid solvent is 0.5 to 10 times weight based on the acetic anhydride.

15. The process for producing a hydrogenated aromatic polycarboxylic anhydride as described in claim 13, wherein the hydrogenated aromatic polycarboxylic acid is 1,2,4,5-cyclohexane-tetracarboxylic acid; and the resulting acid anhydride is 1,2,4,5-cyclohexane-tetracarboxylic dianhydride.

16. A process for producing hydrogenated aromatic polycarboxylic anhydride, wherein in producing an acid anhydride by dehydration reaction of a hydrogenated aromatic polycarboxylic acid, used as the above hydrogenated aromatic polycarboxylic acid is one obtained by feeding an aromatic polycarboxylic acid to a filling bed of a catalyst containing noble metal comprising rhodium or palladium or both of them at a velocity of 1 to 100 weight parts/hr per weight part of the noble metal described above to hydrogenate it at a hydrogen partial pressure of 1 MPa or more by a continuous flow system; and the above hydrogenated aromatic polycarboxylic acid is subjected to dehydration reaction with acetic anhydride of 0.64 to 5.7 times mole based on a carboxyl group of the hydrogenated aromatic polycarboxylic acid, the dehydration reaction being carried out in a glacial acetic acid solvent.

17. The process for producing a hydrogenated aromatic polycarboxylic anhydride as described in claim 16, wherein an amount of the glacial acetic acid solvent is 0.5 to 10 times weight based on the acetic anhydride.

18. The process for producing a hydrogenated aromatic polycarboxylic anhydride as described in claim 16, wherein the hydrogenated aromatic polycarboxylic acid is 1,2,4,5-cyclohexane-tetracarboxylic acid; and the resulting acid anhydride is 1,2,4,5-cyclohexane-tetracarboxylic dianhydride.

19. The process for producing a hydrogenated aromatic polycarboxylic acid as described in claim 1, wherein the aromatic polycarboxylic acid is selected from the group consisting of pyromellitic acid and trimesic acid.

20. The process for producing a hydrogenated aromatic polycarboxylic acid as described in claim 7, wherein the aromatic polycarboxylic acid is selected from the group consisting of pyromellitic acid and trimesic acid.

21. The process for producing a hydrogenated aromatic polycarboxylic anhydride as described in claim 13, wherein the solvent in which the dehydration reaction is carried out includes, in addition to the glacial acetic acid, at least one of hydrocarbons, halogenated hydrocarbons, esters, ketones, ethers and aliphatic acids having a boiling point of at least 50° C.

22. The process for producing a hydrogenated aromatic polycarboxylic anhydride as described in claim 16, wherein the solvent in which the dehydration reaction is carried out includes, in addition to the glacial acetic acid, at least one of hydrocarbons, halogenated hydrocarbons, esters, ketones, ethers and aliphatic acids having a boiling point of at least 50° C.

* * * * *